Feb. 14, 1961 E. S. BOERNER Plant Pat. 2,026
CHRYSANTHEMUM PLANT
Filed May 20, 1960
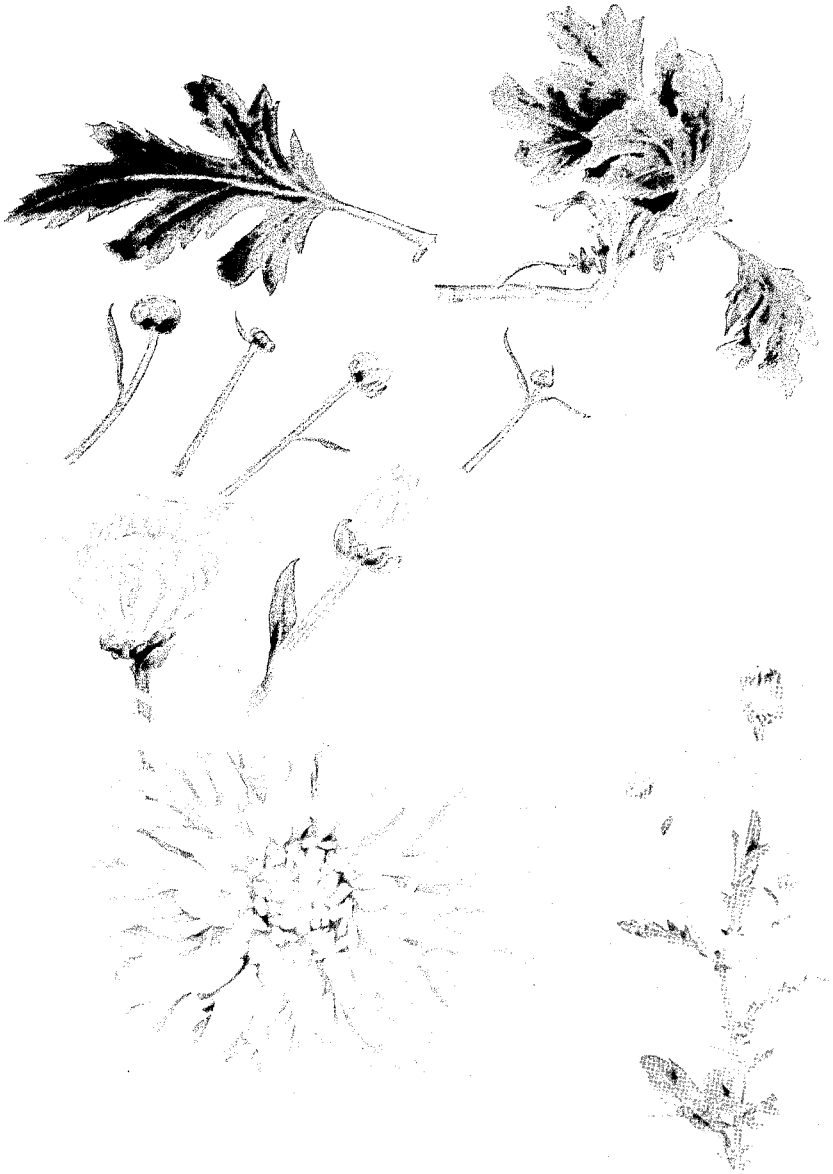
Inventor.
E. S. Boerner
By: Robb & Robb
Attorneys.

United States Patent Office

Plant Pat. 2,026
Patented Feb. 14, 1961

2,026

CHRYSANTHEMUM PLANT

Eugene S. Boerner, Newark, N.Y., assignor to Jackson & Perkins Company, Newark, N.Y., a corporation of New York Filed May 20, 1960, Ser. No. 30,696

1 Claim. (Cl. 47—60)

The present invention relates to a new and distinct variety of chrysanthemum plant of the shaggy decorative class, which was originated by me by crossing an unnamed and unpatented seedling derived from a cross of "Meadowlark" (Plant Patent No. 1,305) × "Thrush" (Plant Patent No. 1,168) with the variety "Cardinal" (Plant Patent No. 1,165).

The primary objective of this breeding was to produce a new chrysanthemum variety having the large flower characteristic and early blooming habit of the unnamed seedling parent referred to above, combined with the red general flower coloring of the parent variety "Cardinal." This objective was fully achieved, along with other improvements, as evidenced by the following unique combination of characteristics which are outstanding in the new variety and which distinguish it from its parents, as well as from all other varieties of which I am aware:

(1) An early blooming habit;

(2) Large bloom size;

(3) A tubular effect of the flower petals at maturity; and (4) A distinctive Carnelian Red general color tonality of the flowers, lightly overcast with Scarlet.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, near mid-afternoon during the early part of the month of October:

Parentage: Seedling.

*Seed parent.*—An unnamed seedling of "Meadowlark" × "Thrush."

*Pollen parent.*—"Cardinal."

Classification: Shaggy decorative.

Growth: Medium tall; vigorous.

Cold resistance: Plants are very winter hardy in northern New York; flowers are frost resistant.

Blooming period: In the Newark, New York climatic area, average date of commencement of bloom is about the end of September, with blooms continuing until frost.

*Flower*

Bud:

*Color.*—When sepals first divide—Massicot Yellow, Plate 16, with upper half of petal lightly overcast with Pale Pinkish Buff, Plate 29. When petals begin to unfurl—Eugenia Red, Plate 13, with lower half of petal lightly overcast with Maize Yellow, Plate 4. When half-blown: inside of petals—Jasper Red, Plate 13, with outer edge of petal Deep Chrome, Plate 3; outside of petals—Nopal Red, Plate 1, lightly overcast with Scarlet, Plate 1, in the lower half of the petal.

*Peduncle.* — Color — Absinthe Green, Plate 31. Strength—strong.

Bloom:

*Size.*—5½ inches.

*Stem.*—Medium strength.

*Form.*—Shaggy decorative.

*Petalage.*—Stiff and curved; petal edges curve downward, giving a tubular effect at maturity.

*Color.*—Center of flower—Deep Chrome, Plate 3, lightly overcast with Coral Red, Plate 13. Outer petals—Deep Chrome, Plate 3, lightly overcast with Carnelian Red, Plate 14. Base of petals—Apple Green, Plate 17. Inside of petals—Carnelian Red, Plate 14, lightly overcast with Scarlet, Plate 1. Reverse of petals—Capucine Buff, Plate 3, lightly overcast with Flesh Color, Plate 14.

*Petals*—Texture—thick. Form—ovoid.

*Fragrance.*—Characteristic chrysanthemum.

*Plant*

Form: Upright; bushy.

Growth: Medium height.

Foliage:

*Size.*—Medium.

*Quantity.*—Normal.

*Color.*—Upper side—Empire Green, Plate 32. Reverse side—Cress Green, Plate 31.

*Texture.*—Leathery.

I claim:

I new and distinct variety of chrysanthemum plant of the shaggy decorative class, substantially as herein shown and described, characterized particularly as to novelty by the unique combination of an early blooming habit, large flower size, tubular effect of the flower petals at maturity, and a distinctive Carnelian Red lightly overcast with Scarlet general color tonality of the flowers.

No references cited.